US006279576B1

(12) United States Patent
Lambert

(10) Patent No.: US 6,279,576 B1
(45) Date of Patent: Aug. 28, 2001

(54) PURIFICATION SYSTEM

(75) Inventor: Hans Lambert, Stockholm (SE)

(73) Assignee: Louis Gibeck, AB, Upplands-Vasby (SE)

( * ) Notice: Subject to any disclaimer, the term of this patent is extended or adjusted under 35 U.S.C. 154(b) by 0 days.

(21) Appl. No.: 09/308,377

(22) PCT Filed: Nov. 18, 1997

(86) PCT No.: PCT/SE97/01932

§ 371 Date: Jun. 30, 1999

§ 102(e) Date: Jun. 30, 1999

(87) PCT Pub. No.: WO98/22173

PCT Pub. Date: May 28, 1998

(30) Foreign Application Priority Data

Nov. 18, 1996 (SE) .................................................... 9604218

(51) Int. Cl.[7] ....................................................... A62B 7/10

(52) U.S. Cl. .................................. 128/205.28; 128/204.18

(58) Field of Search .................... 128/205.28, 205.12, 128/205.22, 204.15, 204.16, 205.11, 202.26, 205.27, 204.18–204.23, 200.24, 205.29, 910, 913; 521/25, 28; 210/870, 728, 718; 95/900; 96/108

(56) References Cited

U.S. PATENT DOCUMENTS

| 3,407,045 | 10/1968 | Temple . |
| 3,498,026 | 3/1970 | Messinger et al. . |
| 3,785,377 | * 1/1974 | Jorgensen ............................ 128/188 |

(List continued on next page.)

FOREIGN PATENT DOCUMENTS 0289446   11/1988   (EP) .

OTHER PUBLICATIONS

Adriani, "The Chemistry and Physics of Anaesthesia", 1 ed., 1979, pp. 151–184, Charles C. Thomas Publishers, Springfield, Illinois, USA.
A.M. Holloway, "Anaesth. Intens. Care", 1994; 22; pp. 359–362.
J.P.H. Fee et al, "Anaesthesia", 1995, vol. 50, pp. 841–845.
"Anaesthesia and Analgesia", 1995, p. 82, Abstract S425.
Fang et al, "Anesth. Analg." 1995; 81:564–8, 1995.
Sperker et al, "Proc. of the 4th European Symp. on Space Environmental and Control Systems", Florence, 21–24 Oct., 1991, pp. 469–472.
Chen et al, "Ind. Eng. Chem. Res.", 1990, 29, 440–447.
Preiss et al., Doc. No. 871515, 1987, Society of Automotive Engineers, In. "Regenerative $Co_2$–control—A Technology Demand for European Manned Sapce Programs".
Woehlck et al, Anesthesiology, V83, No. 1, Jul. 1995, pp. 213–217.
R. Bedford, Anesthesiology, V83, No. 4, Oct. 1995, pp. 33A–34A.
P. Mignon, Doc. Assession No. 11484, The American Society of Mechanical Engineers (ASME Publications), Mar. 29, 1976, "$CO_2$ removal from Submarines Atmospheres by IR–45: Feasibility Study".

(List continued on next page.)

*Primary Examiner*—Aaron J. Lewis
*Assistant Examiner*—Teena Mitchell
(74) *Attorney, Agent, or Firm*—Young & Thompson

(57) ABSTRACT

The invention relates to a regenerative absorber device (20) for the removal of $CO_2$ from expiration gases during anesthesia. The device comprises a container (38) having an inlet (39) for said expiration gases, and an outlet (41) for output gases, the $CO_2$ content of which having been substantially removed therefrom. The device is provided with an ion exchanger (42) having the capability to absorb $CO_2$, disposed in said container (38) such that the gases flow through said ion exchanger from said inlet (39) to said outlet (41). A novel method of anesthesia comprises use of a $CO_2$ absorber device according to the invention.

25 Claims, 8 Drawing Sheets

U.S. PATENT DOCUMENTS

| | | | | |
|---|---|---|---|---|
| 3,814,091 | * | 6/1974 | Henkin | 128/188 |
| 3,898,987 | * | 8/1975 | Elam | 128/145.8 |
| 3,923,057 | | 12/1975 | Chalon . | |
| 4,005,708 | * | 2/1977 | Netteland et al. | 128/142 R |
| 4,596,246 | * | 6/1986 | Lyall | 128/202.27 |
| 4,741,745 | * | 5/1988 | Kadono et al. | 55/43 |
| 4,772,635 | * | 9/1988 | Mitschker et al. | 521/34 |
| 4,963,327 | | 10/1990 | Russell . | |
| 4,989,597 | * | 2/1991 | Werner | 128/203.12 |
| 4,997,803 | * | 3/1991 | Van Der Smissen et al. | 502/400 |
| 5,005,572 | | 4/1991 | Raemer et al. . | |
| 5,007,421 | * | 4/1991 | Stewart | 128/204.18 |
| 5,109,838 | * | 5/1992 | Elam | 128/203.12 |
| 5,113,856 | * | 5/1992 | Van Der Smissen | 128/205.27 |
| 5,147,536 | * | 9/1992 | Engstrom | 210/198.2 |
| 5,368,818 | * | 11/1994 | Cummings et al. | 422/62 |
| 5,411,721 | * | 5/1995 | Doshi et al. | 95/51 |
| 5,428,074 | * | 6/1995 | Cutler | 521/26 |
| 5,466,368 | * | 11/1995 | Arvidsson et al. | 210/198.2 |
| 5,471,979 | * | 12/1995 | Psaros et al. | 128/205.28 |
| 5,487,380 | * | 1/1996 | Grankort | 128/204.15 |
| 5,490,499 | * | 2/1996 | Heinonen et al. | 128/203.28 |
| 5,558,088 | * | 9/1996 | Smith | 128/205.28 |
| 5,566,669 | * | 10/1996 | Komesaroff | 128/205.12 |
| 5,634,426 | * | 6/1997 | Tomlinson et al. | 116/207 |
| 5,642,630 | * | 7/1997 | Abdelmalek et al. | 62/632 |
| 5,678,540 | * | 10/1997 | Kock et al. | 128/205.13 |
| 5,706,830 | * | 1/1998 | Parker | 128/913 |
| 5,849,594 | * | 12/1998 | Balderson et al. | 436/133 |
| 5,886,061 | * | 3/1999 | Beckman | 521/147 |
| 5,917,136 | * | 6/1999 | Gaffney et al. | 95/98 |
| 5,992,413 | * | 11/1999 | Martin et al. | 128/201.13 |
| 6,024,850 | * | 2/2000 | Sampson et al. | 521/25 |
| 6,123,069 | * | 9/2000 | Davis | 128/202.26 |
| 6,123,075 | * | 9/2000 | Kirk | 128/205.13 |

OTHER PUBLICATIONS

"STN International Abstract", Seperation of carbon dioxide from non–acid gases, TEPPER, Frederick et al., DE 2038765 710225.

"STN International Abstract", Stability and equilibrium properties of macroreticular resins for flue gas desulfurization, CHEN, Ten Wen et al., Ind. Eng. Chem. Res. (1990), 29(3), 440–7.

"STN International Abstract", Regenerative CO2–Control—A Technology Demand for European Manned Space Programs, Preiss, Helmut et al., 17th Intersociety Conference on Environmental Systems, SAE, Warrendale, PA, USA, Jul.13–15, 1987.

"STN International Abstract", Apparatus for removing carbon dioxide from polluted air, HIRAO, Masashi; JP 61254219 A2 861112.

"STN International Abstracts", Apparatus for carbon oxides removal from polluted air, TSUDA, Kenji, et al., JP 04200719 A2, 92 07 21.

"STN International Abstract", Apparatus for removing carbon dioxide from polluted air, Hirao, Masashi, JP61254220 A2 861112.

"STN International Abstract", Apparatus for removing carbon dioxide from polluted air, Hirao, Masashi; JP 61254221 A2 861112.

"STN International Abstract", Air purification method, Hirao, Masashi; JP 63252528 A2 881019.

"STN International Abstract", Adsorption apparatus for carbon dioxide removal, Shibata, Kenji; JP 01056114 A2, 80–3–3.

"STN International Abstract", Apparatus for carbon oxides removal from polluted air by adsorption, Tsuda, Kenji; JP 04200720 A2, 920721.

"STN International Abstract", Method for regeneration of basic *ion* *exchange* resin used as adsorbent in apparatus for removal of carbon dioxide from air, Onda, Yukimasa, et al., JP 06134302 A2 940517.

"STN International Abstract", Method for controlled supply of steam to a carbon dioxide adsorption apparatus for regeneration of adsorbent, Onda, Yukimasa, JP 06134303 A2 940517.

* cited by examiner

PURIFICATION SYSTEM

This is the 35 USC 371 national stage of International application PCT/SE97/01932 filed on Nov. 18, 1997, which designated the United States of America.

FIELD OF THE INVENTION

The present invention generally relates to the field of anesthesia, and in particular to purification of expiration gases during anesthesia. In one aspect it relates to a regenerative device for removal of $CO_2$ from such gas, and to methods of regeneration of such a device for multiple use thereof. In other aspects the invention relates to a system of anesthesia and to a method of anesthesia.

BACKGROUND OF THE INVENTION

For the purposes of this application the terms absorption and absorbent will include both absorption and adsorption processes.

It is a well established technique to remove $CO_2$ from expiration gases during anesthesia by means of absorption using mixtures of hydroxides, such as soda lime (a commonly accepted designation of a mixture of sodium and calcium hydroxide). The soda lime is placed in a canister, and expiration gases are passed through the canister, whereby the $CO_2$ reacts to form carbonates, and thus is removed from the expired air. The reason for wanting to remove $CO_2$ is that the anesthetic gases used are expensive and it is desirable to reuse the portion not consumed by the patient. The use of hydroxides has been in practice for more than 80 years since D. E. Jackson designed the first machine to be used in a closed system for anesthesia, and numerous improvements have been described in the literature and patents since then.

It should be noted that the processes occurring in this type of devices are in principle irreversible chemical reactions, where the $CO_2$ and the hydroxides react and carbonates are formed. These carbonates are not easily regenerated such that the hydroxides may be recovered.

DESCRIPTION OF RELATED ART $CO_2$ absorbers based on the use of various hydroxides are extensively reviewed by Adriani in "The Chemistry and Physics of Anesthesia", 1 ed., 1979, pp 151–184, Charles C. Thomas Publishers, Springfield, Ill. USA.

Recently A. M. Holloway in "Anaesth. Intens. Care", 1994; 22; pp 359–362, discussed possible alternatives to soda lime for $CO_2$ removal. Inter alia there is discussed the use of monoethanolamine as a regenerative wet $CO_2$ scrubber, which has been used in submarines. Such systems have the disadvantage that the atmosphere may be contaminated with monoethanolamine and ammonia, and are now being replaced with safer systems. Holloway concludes that $CO_2$ absorption by a molecular sieve is probably the most promising system that could be introduced into anesthetic practice.

J. P. H. Fee et al in "Anesthesia", 1995, volume 50, pp 841–845 describes an efficient system based on a molecular sieve for removal of $CO_2$. In particular the decomposition of sevoflurane to compound A ($CF_2=C(CF_3)OCH_2F$) is discussed, and it is noted that marked decomposition is taking place with soda lime, and a detectable decomposition occurs also with the molecular sieve.

In Anesthesia and Analgesia, 1995, p 82, Abstract S425 the use of molecular sieves is described, and it is stated therein that the sieves also absorbs the anesthetic gases, which of course is not a desirable effect.

As indicated above, at present it appears to be a general view in the art of anesthesia that molecular sieves are the most promising candidate for removing $CO_2$ from expiration air, as an alternative to the well established use of soda lime. None of the workers in the field of anesthesia have acknowledged the prior art dealing with absorption by ion exchange resins as possible candidates in this respect.

There are a number of drawbacks with the use of the absorbent in the form of soda lime or other highly alkaline components.

When the soda lime is used up, it has to be discarded, and the absorbent, possibly containing bacteria or other hazardous micro organisms, is to be regarded as a hazardous waste, and must be treated accordingly. Also the refilling of canisters is a risk operation, in that the granulate being highly alkaline, make a lot of dust that may be irritating to the skin and lungs. Single-use canisters that are not refilled add to the total waste material that has to be discarded.

Another drawback is that the reaction between $CO_2$ and soda lime is exothermic, and depending on the flow rate through the absorbent bed, rather high temperatures may be reached. This may lead to a reaction between the anesthetic and the absorbent with accompanying decomposition of the anesthetic. Especially the occurrence of Compound A (fluoromethyl-2,2-difluoro-I-(trifluoromethyl)vinyl ether; $CF_2=C(CF_3)OCH_2F$) is a serious risk factor. The formation of compound A is also observed with the absorbent Baralyme™ (see Anesth. Analg. 1995;81:564–8).

Another highly toxic by-product is carbon monoxide which is believed to be formed from the reaction of anesthetics such as desflurane, enflurane, and isoflurane with desiccated carbon dioxide absorbents of the prior art. With respect to the above consideration, replacement of carbon dioxide absorbent with fresh product is recommended whenever desiccation is suspected. Desiccation is believed to result from high fresh gas flows passing through the carbon dioxide absorber canister over the course of a weekend. In the case of the present invention these problems are eliminated by the use of absorber material of the ion exchange type on which no such reactions take place. The above mentioned problems do not arise with the absorber of the present invention.

A further drawback associated with the use of a molecular sieve for $CO_2$ absorption is that molecular sieves also absorbs a substantial amount of the anesthetic gases.

Also, of course the irreversible nature of the soda lime based devices is a fundamental drawback, which is overcome by the invention.

SUMMARY OF THE INVENTION

An object of the present invention is therefore to provide a method and device for removing $CO_2$ from expired air from a patient subject to anesthesia, where the active substance for $CO_2$ removal is an ion exchange resin. The device shall be regenerative such that the hazardous handling of contaminated spent material and highly alkaline soda lime is eliminated.

The device will have a capability of being regenerated 20 times while maintaining 90% of its activity, preferably 95 times with 90% activity, and 200 times with more than 50% activity left.

The inventors have now surprisingly discovered that it is possible to design a regenerative $CO_2$ removal system for anesthetic applications, without the prior art disadvantages, and making use of the capacity of ion exchange materials as absorbent. This is in contrast toithe general opinion in this field, that molecular sieves be the most promising option as a substitute for the soda lime based technology.

A very important advantage of the invention is that anion exchange resins do not exhibit the above mentioned behavior of molecular sieves, namely to absorb a substantial amount of the anesthetic gases that are passed through such resins.

The above object is thus achieved with a regenerative $CO_2$ absorbing device a system for anesthesia and a method of anesthesia as recited in the claims.

Methods and an apparatus of regeneration of a $CO_2$ absorber is also defined in the claims.

Various embodiments of the different aspects of the invention are defined in the dependent claims.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus not limitative of the present invention, and wherein.

DETAILED DESCRIPTION OF PREFERRED EMBODIMENTS

Figure 1:
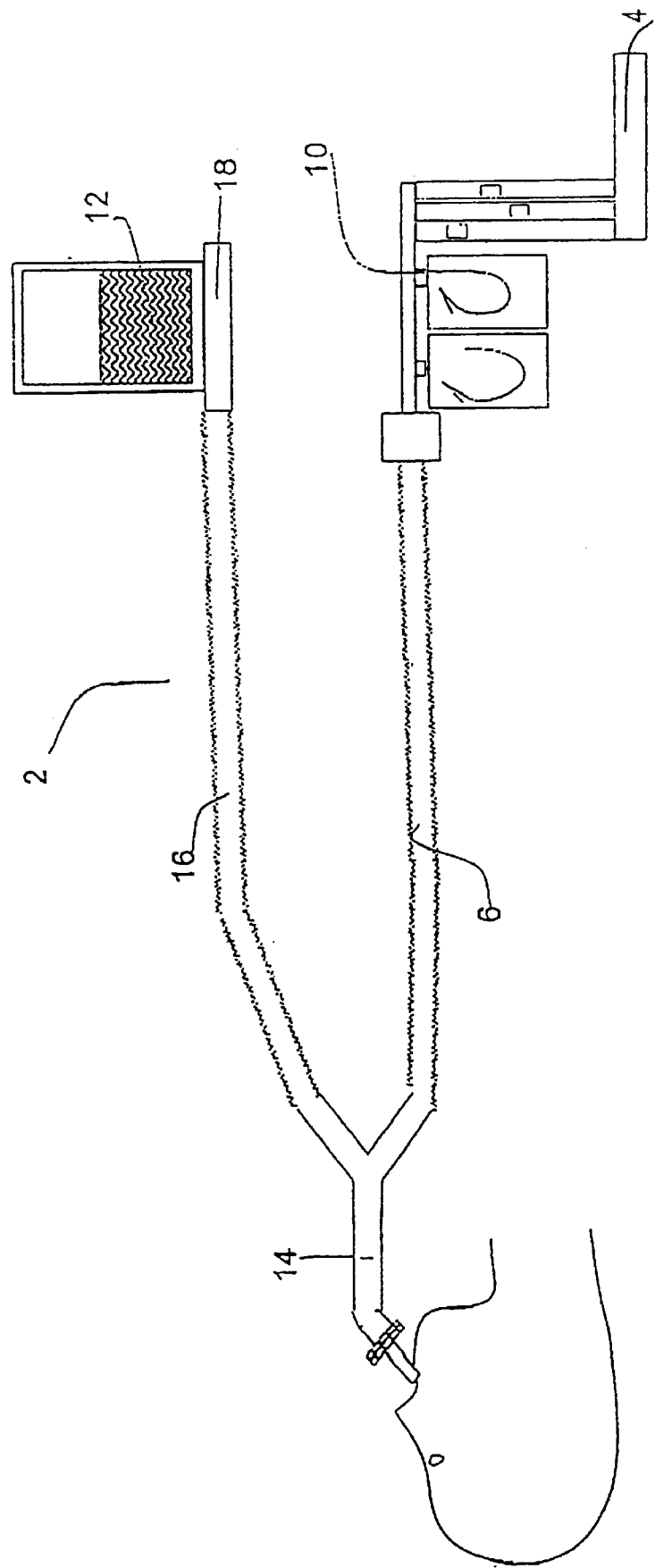
FIG. 1 is an overview of an anesthetic system in general.

With reference to FIG. 1 the general design of an anesthetic system is described.

Such a system, generally designated with reference numeral 2, comprises a source 4 for gas,(commonly oxygen, nitrous oxide and/or air), from which the gas is conveyed via a tubing system 6 to the patient, via an anesthetic vaporizer comprising a gas mixer 10. In order to facilitate the patient's breathing during anesthesia, the anesthetic systems also comprise a pump 12. This may be anything from a sophisticated ventilator to a simple rubber bladder, the latter being compressed manually. The expired air is passed from the patient via a so called Y-piece 14 through a tubing system 16 to a gas vent 18. Such a system is referred to as an open anesthetic system.

Figure 2:
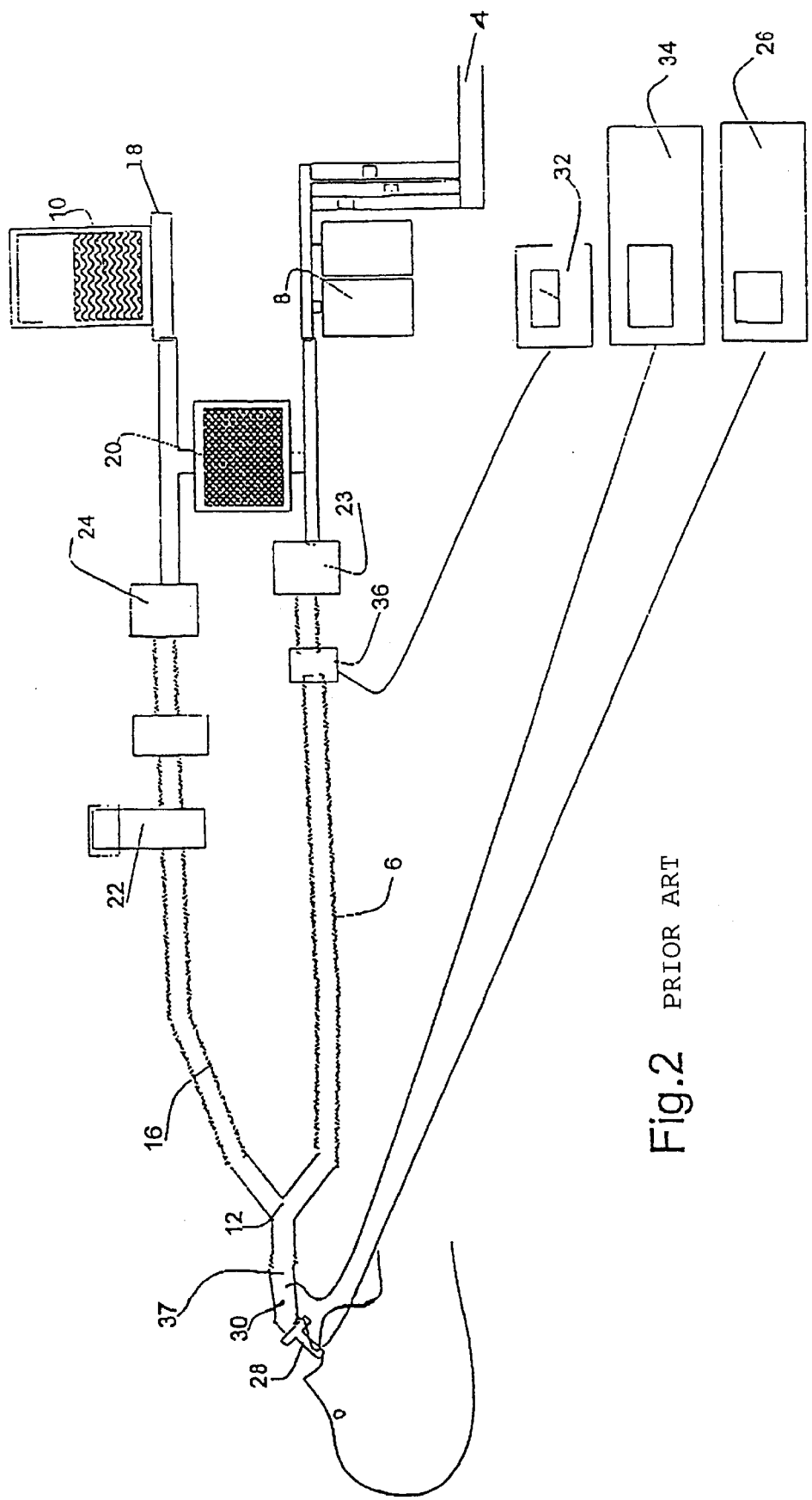
FIG. 2 is an overview of an anesthetic system incorporating a $CO_2$ absorber unit of the invention.

A disadvantage with an open system is that a large amount of expensive gas is consumed, and therefore one often uses a so called recirculating anesthetic system, a schematic illustration of which is shown in FIG. 2. In addition to the components common to the open system of FIG. 1 (like parts designated with like numerals), a recirculating system comprises a so called $CO_2$ absorber 20, the function of which is to absorb $CO_2$ from the expired air. The absorber 20 is disposed to interconnect the tubing 16 on the expiration side and the tubing 6 on the inspiration side, such that expired air may be diverted and passed through the absorber, and returned to the patient after having been freed from $CO_2$. The system also comprises a number of valves. A PEEP valve 22 is provided in the expiration tubing 16, and is used for limiting the pressure inside the lungs. A one-way valve 24 provided after the valve 22, and another one-way valve 23 provided in the inspiration tubing 6, immediately after the $CO_2$ absorber, are basically provided for directing the circulating gases. A gas exhaust is venting a minor portion of the gas from the system.

There is also provided a number of monitors, e.g. a gas monitor 26, showing the gas concentrations, and having sensing means 28 located at a mouth piece 30, an oxygen monitor 32 and a $CO_2$ monitor 34, the sensing means 36 and 37 respectively of which being located in the inspiration tubing after the $CO_2$ absorber 20.

Prior art systems of the kind illustrated in FIG. 2 are provided with a $CO_2$ absorber unit containing soda lime as the active agent.

Reference is made to the book by Adriani for further details on this type of prior art systems.

Figure 3:
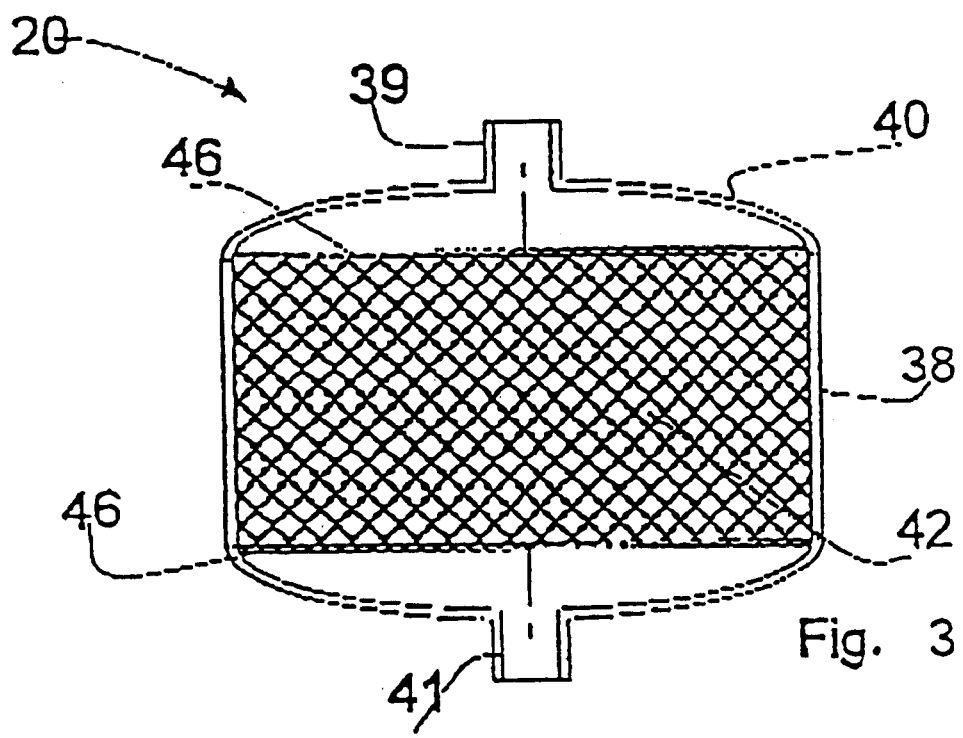
FIG. 3 shows an absorber unit of the invention in detail.

Turning to FIG. 3, a regenerative CO2 absorber device according to the invention will now be described. The absorber according to the invention may be used in the system of FIG. 2 without any significant changes to the system.

The absorber unit, generally designated 20, comprises a container or canister 38, made of metal or plastic material, and is provided with a lid 40. Thee container 38 is provided with an inlet member 39, connectable to the expiration tubing 16 of an anesthetic system, and an outlet member 41 connectable to the inspiration tubing 6 of said system. In a first embodiment the canister is simply filled with an ion exchanger resin 42 in the form of small spherical beads or granules of essentially uniform size.

In view of the chemistry of $CO_2$ absorption, the ion exchanger is preferably of the anion type. A preferred composition is a weak anion exchanger comprising a tertiary amine on a cross-linked acrylic polymer support. Such ion exchangers are well known and commercially available, and as such they do not form part of the invention.

Figure 4:
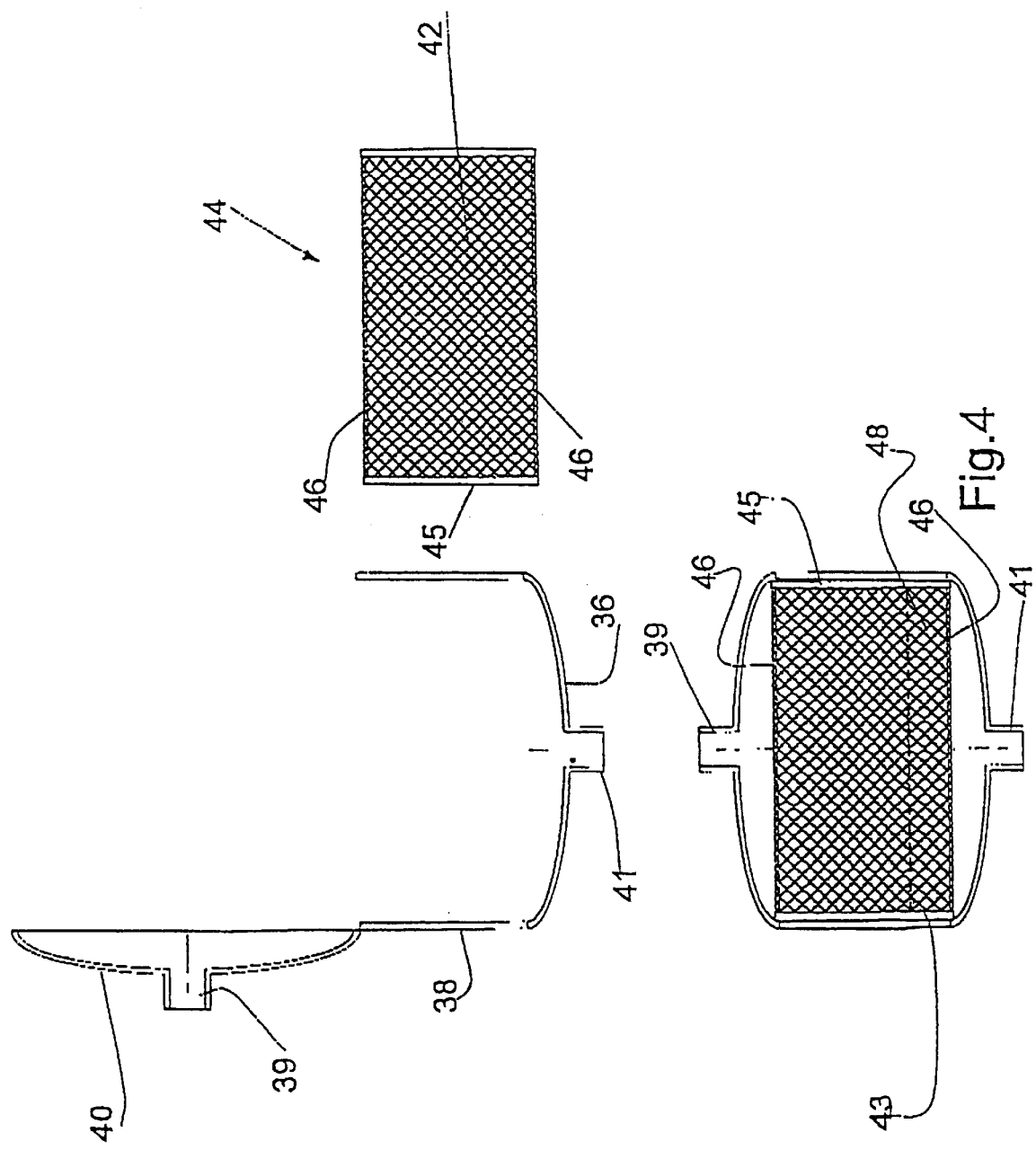
FIG. 4 shows a canister for an absorber unit and a replaceable cassette containing the ion exchanger.

In a second embodiment the ion exchanger beads are disposed inside a cassette or cartridge 44, fitting inside said canister 38 in a removable fashion, as shown in FIG. 4. The cassette 44 may be comprised of a cylinder 45 of metal or a suitable plastic material, such as polypropylene. An important property of such a material is that it should be able to withstand temperatures of at least 120–130° C., that are experienced during regeneration (to be described later). In order to confine the ion exchanger particles or beads 42 inside the cassette 44, covers in the form of a mesh 46 of e.g. sintered polypropylene or metal may be provided. Other materials capable of permitting steam and other gases to permeate may be utilized.

As is shown in FIG. 4, the canister is provided with a lid 40 that may be hinged to the container part. Of course the lid may be secured by other means, such as threads, clamps etc. There should also be provided appropriate sealing means between the canister and the lid, e.g. an O-ring provided along the periphery of the canister. In a preferred embodiment the container 38 is relatively wide and low, to provide for a low flow resistance. It should have the capacity to hold about 2 kg of ion exchanger, although the capacity of course it is not restricted in any way, but may be adapted to a specific application. It should be recognized that the size of the ion exchanger beads have an influence on the flow resistance in the absorber unit. However, it will be a matter of ordinary practice for the man skilled in the art to design the canister in terms of its dimensions for a specific bead size and amount of the ion exchanger.

Regarding suitable ion exchangers, in general, weak basic anion exchange resins are suitable as the absorber agent in the present invention. Such resins have primary, secondary and/or tertiary, functional active amine groups, attached to a polymeric matrix. Generally, the polymeric matrix can be a polystyrene, a polystyrene-divinyl benzene copolymer, a phenolformaldehyde, a polyacrylic acid, a polymethacrylic acid-divinylbenzene copolymer or an epoxy type polymer. A large number of these resins are commercially available and can be used in the invention, although with different degrees of applicability.

In particular macroporous ion exchanger resins are suitable, because they exhibit a large active surface, and provide good flow properties. The macroporosity is provided by the polymer matrix.

Preferred, weak, basic, anion exchange resins, having a particularly high affinity to and capacity for absorbing carbon dioxide, can be repeatedly regenerated, without a substantial loss of their absorption characteristics, including such resins in which the active group displays a polyamine functionality and contains at least one secondary amine nitrogen atom. Such materials are prepared by reaction of an addition polymer and condensation polymer, respectively, with polyfunctional amines, having one secondary amine nitrogen atom, such as for example diethylene triamine, triethylene tetraamine and tetraethylene pentaamine. Such preferred resins comprise polyacrylic acid-polyamine resins, which are prepared according to the disclosure of U.S. Pat. No. 2,582,194 and epoxy-polyamine resins commonly prepared through reaction of an epoxy resin and a polyamine in a solvent such as xylene.

Polystyrene-divinylbenzene copolymers of gel resin type exhibits polyamine functional groups and are particularly useful as absorber agents. Resins of this type can be produced through reaction of chloromethylene (chloromethylated)-styrene divinylbenzene copolymer with an amine such as diethylene triamine, triethylene tetraamine, tetraethylene pentaamine and other polyfunctional amines. An equimolar amount and an excess, respectively, of amine for each chloromethylene group, causes a condensation of a chloromethylene group with an amine group, such as through the following depicted reaction using diethylenetriamine:

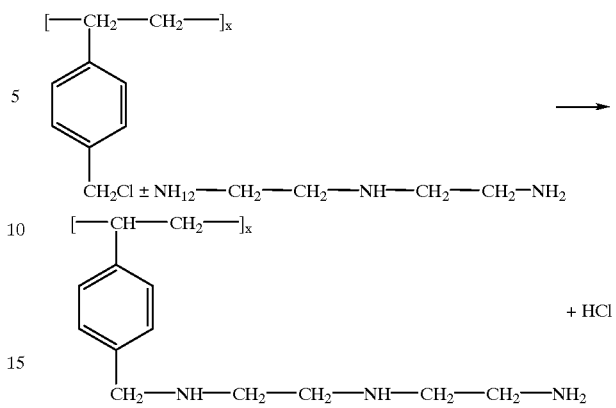

When the ratio of amine is about ½ the equimolar ratio, one further cross-link and essentially one secondary amine functionality is favored through the condensation as represented by the following equation:

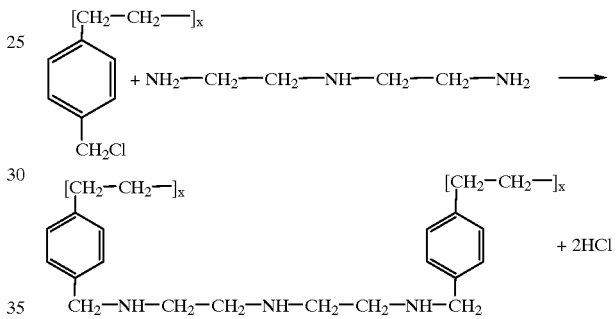

The carbon dioxide capacity of this resin type is relative to the ion exchange capacity, and common methods for improving the ion exchange capacity also improves the dynamic carbon dioxide capacity. To obtain a suitable porosity, copolymers are preferably used containing less than about 10% divinylbenzene, preferably 3 to 5%. Amberlite IR-45, a chloromethylene-polystyrene-divinylbenzene copolymer (chloromethylated polystyrene-divinylbenzene copolymer), to which diethylene triamine is added, represents a typical commercially available resin of this type.

Examples of other suitable weak basic anion exchange materials available from Bayer are the following Lewatit ion exchange materials, S 3428, S 4328, S 5428 and S 6328.

The Lewatit line of ion exchangers are tertiary amines, which are stable, as opposed to primary and secondary amines which undergo degradation more easily.

Another suitable, commercially available product is AMBERLITE IRA67, available from Rohm & Haas. However, it is conceived that practically any anion exchangers are usable with the invention, some with better performance than others, in terms of ability to absorb $CO_2$, stability in use and capability of undergoing regeneration.

Figure 5:
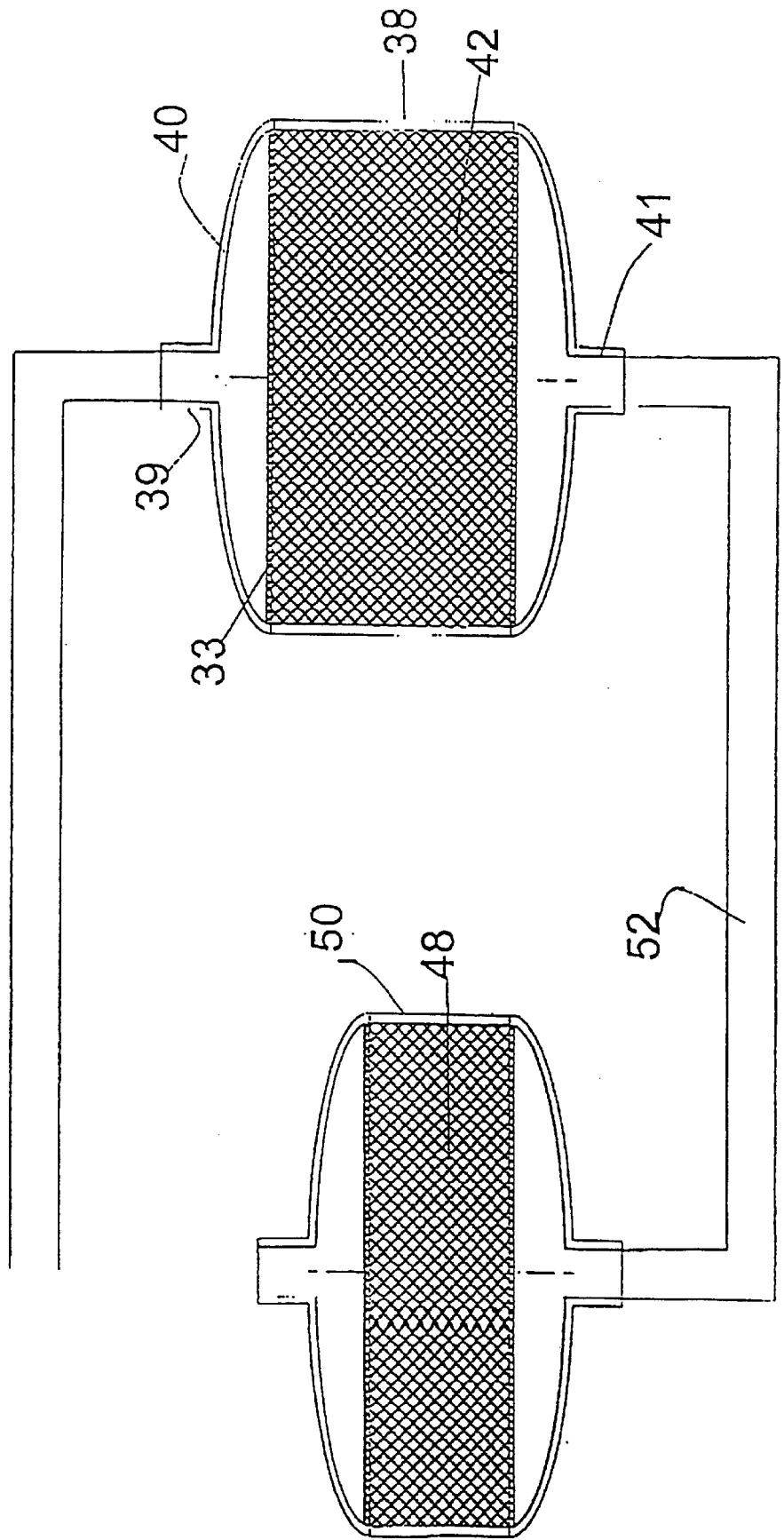
FIG. 5 shows an absorption unit having a separate cation exchanger unit in line with the anion exchanger unit.

One possible risk factor in connection with the use of anion exchangers is that the anion exchangers may release minute amounts of free amines, representing a health risk. In order to eliminate the released amines from the flow of inspiration gases, there may be provided a cation exchanger in the flow path. One embodiment of the absorber unit wherein a cation exchanger 48 is provided in a separate container, is shown in FIG. 5. By separating the two types of ion exchanger in this fashion it is possible to replace only the material that actually has been used up.

In FIG. 5, there is disclosed an embodiment of an absorber unit comprising an anion exchanger 42 in one canister 38 and a cation exchanger 48 in another canister 50, the canisters 38 and 50 being connected in series via tubing 52. The cation unit is connected downstream of the anion unit in order to be able to eliminate traces of free amines that may be released from the anion exchanger, as mentioned above.

However, it is equally possible to dispose the cation and anion exchangers inside the same container. In such a case the two types of ion exchangers may be placed in separate layers, separated by a separator means 43 (indicated with a dashed line in FIG. 4), such as a mesh like the one previously mentioned, or made of other gas permeable materials. It is also conceivable to mix the anion and cation exchangers homogeneously inside the canister.

Of course the embodiment shown in FIG. 5 is more costly because of its higher degree of constructional complexity, but has the advantage that the cation and anion exchanger resins may be regenerated separately.

The amount of cation exchanger may be from 1/10 of the amount of anion exchanger up to equal amounts of both types.

The ion exchanger may also contain an indicator, e.g. dyes which change color as a function pH. Methyl Orange, phenolphthalein and ethyl violet are examples of indicators showing when the ion exchanger has been essentially used up (see also Adriani p 176, and U.S. Pat. No. 5,005,572). The skilled man would easily find other suitable indicators, given what components the system according the invention is comprised of.

Now regeneration of the absorber units will be described with reference to FIGS. 6 and 7 wherein two embodiments of an in-line regeneration system is shown, and FIG. 8 wherein a "stand-alone" apparatus for regeneration is shown.

Regeneration is accomplished by removing the carbon dioxide absorbed on the ion exchange resin, and can be accomplished in various ways. Wet regeneration would involve passing a base, for example sodium hydroxide in aqueous solution through the absorbent bed, whereby the carbon dioxide is removed in the form of sodium bicarbonate dissolved in water. Other bases could also possibly be used for wet regeneration of the ion exchange material. Also contemplated is regeneration by means of heating, with the ion exchange material being heated by an internal or external heating source and a gas supplied passing through the ion exchanger bed. Regeneration can also be achieved by applying a reduced pressure or vacuum to the ion exchanger material, with or without heating of said ion exchanger. The presently preferred method is to pass steam through the absorbent.

Figure 6:
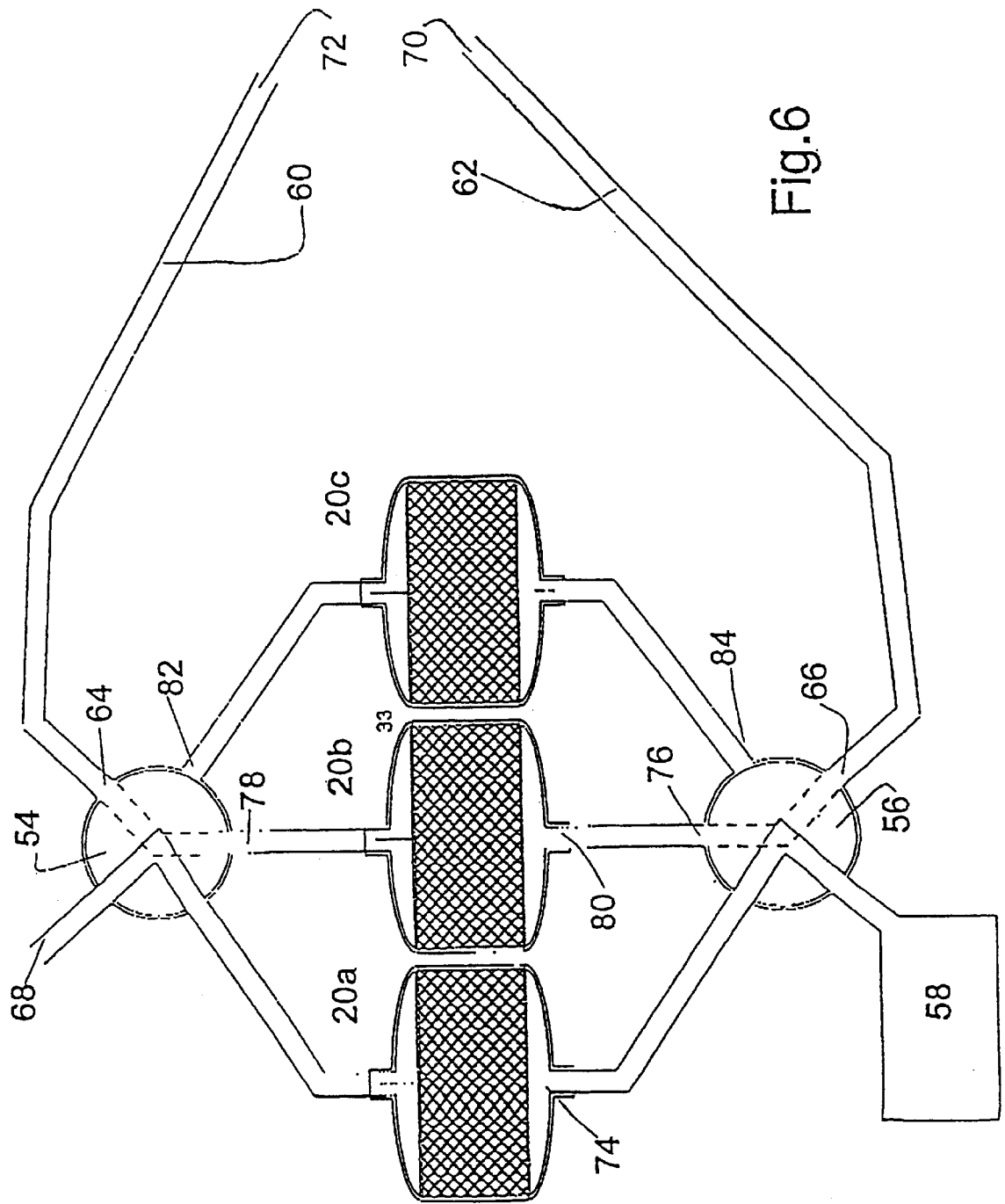
FIG. 6 is an overview of an in-line regeneration set-up of the invention with three absorber units.

Referring to FIG. 6, a set-up for regeneration in-line with an anesthetic system is depicted comprising three absorber units 20a, 20b, 20c. These units are connected in parallel via tubing to two valves, 54 and 56 respectively. Valve 54 is connected to the downstream side of each absorber unit and valve 56 to the upstream side. A steam generating device 58 is provided and is connected to valve 56. Via tubing 60 and 62 attached to the valves 54 and 56 at 64 and 66 respectively, the set-up is also connected to an anesthetic system, such as the system shown in FIG. 2, where it replaces the absorber unit 20. Valves 54 and 56 are two similar 5-port valves through which two separate flows can occur simultaneously, a first regeneration flow of steam coming from the steam generator 58 and being vented at a vent 68, and a second flow of anesthetic gases entering at inlet 70 and leaving at outlet 72. The valves 54 and 56 are adjustable so that there are provided all possible combinations of flow paths required for simultaneous regeneration and utilization during anesthesia. The absorber units of the system in FIG. 6 are each capable of being operated in three modes, namely usage, regeneration, and stand-by mode. In FIG. 6 the valves are switched to such positions that the regeneration steam from steam generator 58 is passed to inlet 74 to regenerate the ion exchanger resin in the absorber unit 20a connected thereto. Another absorber unit 20b is connected via valve outlet 76 and valve inlet 78 respectively, to the anesthetic system in which said absorber is being used, with the anesthetic gases entering the absorber unit 20b at 80. The unit 20c connected to valves 54 and 56 at 82 and 84 respectively, in which the ion exchange resin already has been regenerated, is closed off from both flows, and waiting in stand-by mode. Thus, by setting the valves 54 and 56 appropriately, the absorber units can be inter-changeably connected to regeneration, usage and stand by mode.

Figure 7:
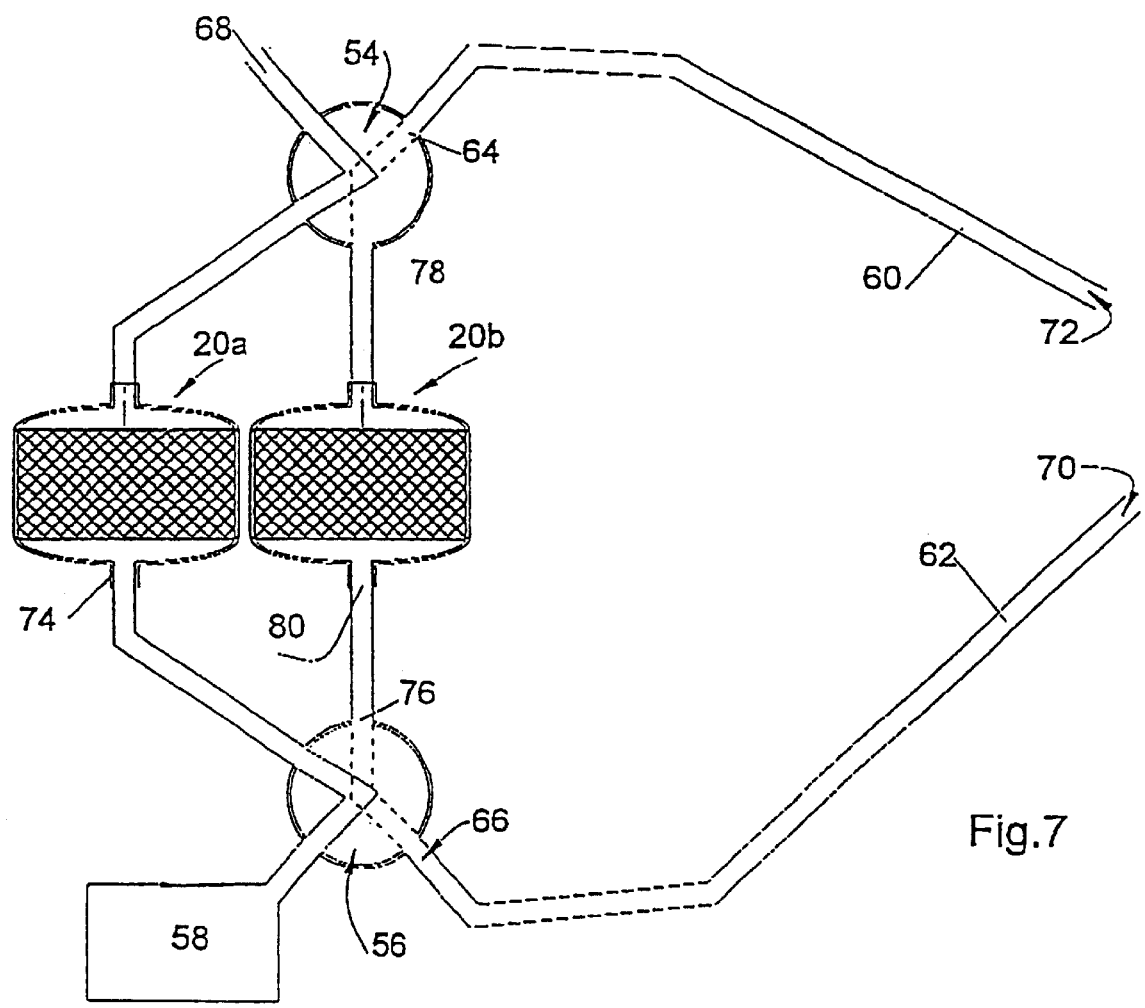
FIG. 7 is an overview of an in-line regeneration set-up of the invention with two absorber units.
Figure 8:
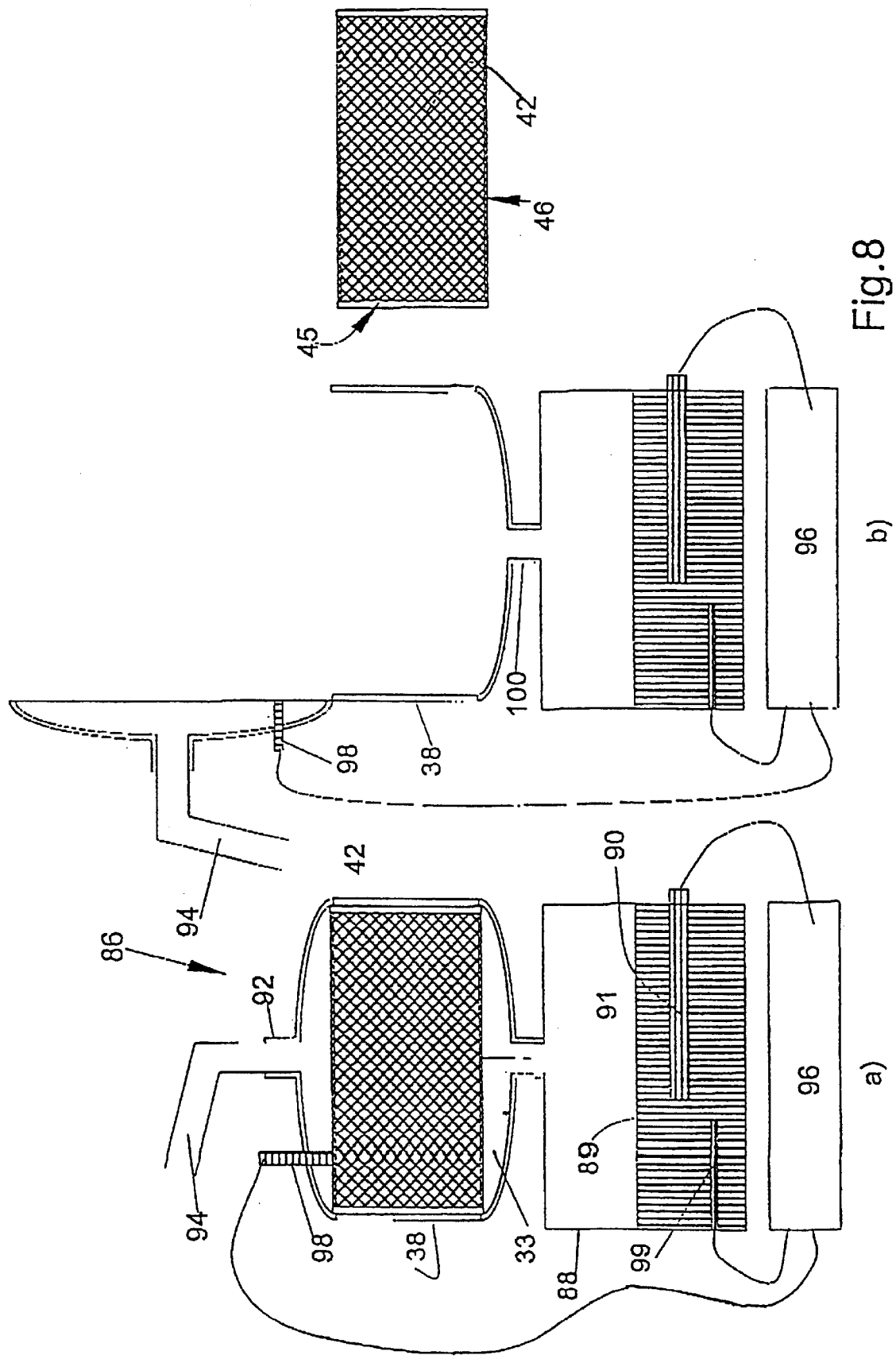
FIG. 8 is an overview of a stand-alone regenerator for regenerating individual absorber cassettes.

FIG. 7 shows a set-up for regeneration similar to the above described apart from including only two absorber units which alternately can be connected to usage and regeneration mode. While this set-up does not allow for the same high security as the one in FIG. 6, it provides a lesser degree of complexity and is less bulky. Similarly, more than three units can be set-up as above, having one or more functioning in parallel or sequentially in like or different modes.

In FIGS. 8a and 8b, a separate regeneration device 86 is shown, in closed state (FIG. 8a), and in an open state (FIG. 8b) with an ion exchanger cassette removed. The device comprises a first container 88 for water 89 equipped with a heating device 90, said container 88 being connected at its top to a second container 38 in which the ion exchange material 42 is to be placed for regeneration. On top of the second container an outlet 92 is provided equipped with venting tubing 94. The container 38 may be designed essentially equal to the canister of an absorber unit 20. Heating is controlled by a heating control means 96, which is connected to a temperature sensor 98 disposed at the top of the absorber container, and to a second temperature sensor 99 provided in contact with the water 89 in container 88. During regeneration, steam emerging from the headspace of container 88 into absorber container at inlet 100, moves through the ion exchanger material. The steam entering the absorber container through inlet 100 heats the ion exchanger material and forms a temperature front in the material, said front gradually moving upwards through the material. As the front reaches the upper surface of the ion exchanger material the front is sensed by temperature sensor 98 indicating a temperature rise, and thus that regeneration is completed, Optionally vacuum can be applied to the regeneration device 86 via venting tubing 94. By applying a vacuum the boiling point of the water can be lowered, and by a decrease of the boiling point by 20° C. it is estimated that the duration of the ion exchanger material can be prolonged by 4 times.

Next, a method of anesthesia according to the invention will be described.

A patient to be anaesthetized will be subject to standard preparations for anesthesia, and indeed from the patient's point of view, there will be no differences in experience.

Thus, a patient to be anaesthetized is supplied at a controlled rate with a suitable inspiration gas mixture containing an anesthetic agent. During the process, expiration gases are pumped away at a rate, appropriate for maintaining a controlled flow of inspiration gases to the patient. From the expiration side, at least a portion of the expiration gases from the patient is passed through an ion exchanger for substantially removing $CO_2$ therefrom. The gas, having been substantially freed from $CO_2$, is thereafter recirculated to the flow of inspiration gases. Preferably the ion exchanger is an anion exchanger. Suitably said expiration gases are also passed through a cation exchanger. In a preferred embodiment of the method of the invention, said expiration gases are passed through said anion exchanger and said cation exchanger in sequence, beginning with the anion exchanger.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claim is:

1. A regenerative absorber device for the removal of $CO_2$ from $CO_2$ containing expiration gases during anaesthesia, comprising
   a container having an inlet for said $CO_2$ containing expiration gases, and an outlet for output gases, whereby the $CO_2$ has been substantially removed from said gases; and
   a weak basic anion exchanger having the capability to absorb $CO_2$, and disposed in said container in such a way that the gases will flow through said anion exchanger from said inlet to said outlet.

2. The device according to claim 1, wherein the anion exchanger is in the form of a bed of anion exchange resin, said resin comprising uniform, spherical beads.

3. The device according to claim 2, further comprising a pH indicator means for visibly indicating when the anion exchange resin has been essentially used up.

4. The device according to claim 1, further comprising a cation exchanger bed.

5. The device according to claim 4, further comprising a partition separating the beds.

6. The device according to claim 4, wherein at least one of said anion exchanger and cation exchanger comprises a cassette removably disposed in the respective container.

7. The device according to claim 6, wherein each cassette is made of a material capable of withstanding temperatures at least in the range 120–130° C.

8. The device according to claim 1, further comprising a second container containing a cation exchanger, fluidly connected to the outlet of said container containing the anion exchanger.

9. A recirculating system for anaesthesia, comprising
   supply means for supplying an anaesthetic gas;
   inspiration tubing means provided on an inspiration side of said system and fluidly connected to said supply means for passing anaesthetic gas to a patient;
   expiration tubing means provided on an exhalation side of said system for removing exhalation gases from said patient;
   said inspiration and expiration tubing means being connected to a mouthpiece for insertion in the patient's mouth; and
   at least one regenerative absorber device for removing $CO_2$ from said exhalation gases; said device comprising a container containing a weak basic anion exchanger, said container having an inlet connected to the expiration tubing means on the exhalation side, and an outlet connected to the inspiration tubing means on the inspiration side such that exhaled gases are divertable through said absorber device, and returned to the patient after having been freed from $CO_2$.

10. The system according to claim 9, comprising at least two absorber devices, fluidly connected to the system in parallel by means of multiple-path valve means, such that while one absorber device is in operation in the system, at least one other absorber device is being regenerated, or is in stand-by condition.

11. The system according to claim 10, further comprising a regeneration apparatus for regenerating the anion exchanger; said regeneration apparatus comprising steam generator means; means for passing steam from said steam generator means through said anion exchanger; detecting means operatively associated with said anion exchanger for detecting when said anion exchanger has been completely penetrated by steam from said steam generator; and multiple-path valve means for selectively connecting a selected absorber device to said regeneration apparatus for regenerating said selected absorber device.

12. The system according to claim 9, further comprising a gas monitor having sensing means located at said mouthpiece; an oxygen monitor having sensing means located in the inspiration tubing means; and a $CO_2$ monitor having sensing means located in the inspiration tubing means after the absorber device.

13. A method of regenerating an absorber device for removing $CO_2$ from $CO_2$ containing expiration gases, the device including a container containing a weak basic anion exchanger, the method comprising passing steam through said anion exchanger, optionally under reduced pressure to regenerate said absorber device.

14. A method of regenerating an absorber device for removing $CO_2$ from $CO_2$ containing expiration gases, the device including a container containing a weak basic anion exchanger, the method comprising passing alkaline medium through the anion exchanger, either while still inside the container, or removed from the container and placed in a separate regenerator vessel.

15. The method according to claim 14, wherein said alkaline medium is an aqueous solution of a hydroxide.

16. A method of regenerating an absorber device for removing $CO_2$ from $CO_2$ containing expiration gases, the device including a container containing a weak basic anion exchanger, the method comprising the step of heating the anion exchanger and passing a gaseous medium therethrough, carrying liberated $CO_2$ with said gaseous medium.

17. A method of regenerating an absorber device for removing $CO_2$ from $CO_2$ containing expiration gases, the device including a container containing a weak basic anion exchanger, the method comprising subjecting the anion exchanger to vacuum conditions such that $CO_2$ is liberated, optionally with heat applied.

18. An apparatus for regenerating an absorber device for removing $CO_2$ from $CO_2$ containing expiration gases, said device including a container containing a weak basic anion exchanger, said container having an inlet for said $CO_2$ containing gases, and an outlet for output gases, the apparatus comprising
   steam generator means;
   means for passing steam from said steam generator means through said anion exchanger; and
   detecting means operatively associated with said anion exchanger for detecting when said anion exchanger has been completely penetrated by steam from said steam generator.

19. The apparatus according to claim 18, further comprising means for connecting the inlet of the absorber device directly to said steam generator means and the outlet of said device to a venting means.

20. The apparatus according to claim 19, further comprising vacuum means for creating a vacuum in the apparatus, said vacuum means being connected to the venting means.

21. The apparatus according to claim 18, wherein said detecting means comprise a temperature sensor provided at the top surface of said anion exchanger enclosed in said container, said temperature sensor being structured and arranged to detect a temperature increase at the top surface of said anion exchanger.

22. The apparatus according to claim 18, wherein said steam generator means comprise a container for water, a heating means, and temperature control means.

23. A method of anaesthesia, comprising:
supplying at a controlled rate a suitable inspiration gas mixture containing an anaesthetic agent, to a patient to be anaesthetized;
pumping away expiration gases at a suitable rate, for maintaining a controlled flow of inspiration gases to the patient;
passing at least a portion of said expiration gases through a weak basic anion exchanger for substantially removing $CO_2$ therefrom; and
recirculating the portion of expiration gases, now freed from $CO_2$, to the flow of inspiration gases.

24. The method according to claim 23, further comprising passing the expiration gases through a cation exchanger.

25. The method according to claim 24, wherein said expiration gases are first passed through said anion exchanger, and then through said cation exchanger.

* * * * *